US00PP28992P2

(12) United States Plant Patent
Lim

(10) Patent No.: US PP28,992 P2
(45) Date of Patent: Feb. 27, 2018

(54) ***ROSA* PLANT NAMED 'LIMBIRD'**

(50) Latin Name: *Rosa hybrida*
Varietal Denomination: LIMbird

(71) Applicant: Peter Ping Lim, Escondido, CA (US)

(72) Inventor: Peter Ping Lim, Escondido, CA (US)

(73) Assignee: Altman Specialty Plants, Inc, Vista, CA (US)

( * ) Notice: Subject to any disclaimer, the term of this patent is extended or adjusted under 35 U.S.C. 154(b) by 0 days.

(21) Appl. No.: 15/330,568

(22) Filed: Oct. 13, 2016

(51) Int. Cl.
*A01H 5/02* (2006.01)

(52) U.S. Cl.
USPC ..... Plt./147

(58) Field of Classification Search
USPC ..... Plt./147
See application file for complete search history.

*Primary Examiner* — Annette H Para
(74) *Attorney, Agent, or Firm* — Cassandra Bright

(57) ABSTRACT

A new and distinct garden floribunda *Rosa* cultivar named 'LIMbird' is disclosed, characterized by distinctive apricot colored flowers. Plants are dwarf, vigorous and can be grown on their own roots. Plants exhibit good resistance to blackspot diseases. The new variety is a *Rosa*, normally produced as an outdoor garden or container plant.

1 Drawing Sheet

Latin name of the genus and species: *Rosa hybrida.*
Variety denomination: 'LIMbird'.

BACKGROUND OF THE INVENTION

The new *Rosa* cultivar is a product of a planned breeding program conducted by the inventor, Peter Ping Lim. The objective of the breeding program was to produce vigorous new garden floribunda rose varieties for ornamental commercial applications. The cross resulting in this new variety was made sometime between April and June of 2009.

The seed parent is the unpatented variety *Rosa* 'Survivors'. The pollen parent is unknown. The new variety was selected in June of 2010 by the inventor in a group of seedlings resulting from the 2009 crossing, in a research nursery in McMinnville, Oreg.

Asexual reproduction of the new cultivar was performed by vegetative cuttings. This was first performed at a research greenhouse in McMinnville, Oreg. in June 2010 and has shown that the unique features of this cultivar are stable and reproduced true to type in more than 5 successive generations.

SUMMARY OF THE INVENTION

The cultivar 'LIMbird' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LIMbird' These characteristics in combination distinguish 'LIMbird' as a new and distinct *Rosa* cultivar:

1. Compact dwarf floribunda rose with a vigorous plant habit.
2. Heat tolerance.
3. Continuous flowering.
4. Apricot flower coloration.
5. Early flowering.

6. Can be grown without grafting, performs vigorously on its own roots.
7. Easy to propagate and root.
8. Resistance to black spot disease.

Plants of the new cultivar 'LIMbird' are similar to plants of the seed parent, in most horticultural characteristics, however, plants of the new cultivar 'LIMbird' differ in the following:

1. The seed parent has a hot pink flower, the new variety has an apricot colored flower.
2. The seed parent is a hybrid tea, the new variety is a floribunda.
3. Flowers of the seed parent are larger.

COMMERCIAL COMPARISON

Plants of the new cultivar 'LIMbird' can also be compared to the commercial variety *Rosa* 'Heritage', unpatented. These varieties are similar in most horticultural characteristics, however 'LIMbird' differs in the following:

1. Plant habit of the new variety is dwarf and bushy, plant habit of 'Heritage' is upright.
2. The new variety has a smaller flower.
3. The new variety is more heat resistant than this comparator.
4. The new variety is less fragrant than 'Heritage'.

BRIEF DESCRIPTION OF THE PHOTOGRAPH

The accompanying photograph in FIG. 1 illustrates in full color a close up of an individual flower.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'LIMbird' plants grown outdoors, in Palm Desert, Calif. The growing temperature ranged from approximately 10° C. to 38° C. during the day and from approximately 5° C. to 22° C. during the night. Measurements were taken in September. General light conditions were very bright, normal sunlight. Measurements and numerical values represent averages of typical plant types.

Botanical classification: *Rosa* 'LIMbird'.

PROPAGATION

Time to initiate roots: About 15 days at approximately 20° C.

Time to produce a rooted cutting: About 35 days at approximately 20° C.

PLANT

Age of plant described: Approximately 2 years.
Growth habit: Compact spreading.
Container size: 2 gallon.
Height: 38 cm.
Plant spread: 38 cm.
Rootstock: Own root.
Growth rate: Moderate.
Branching characteristics: Sympodial branching.
Length of primary lateral branches: Average 12 cm.
Diameter of lateral branches: Approximately 7 to 9 mm.
Quantity branches: 6 to 8 main branches, abundant lateral branches, 10 to 20 lateral branches per main branch.

Branches—young wood:
- *Diameter*.—Approximately 3 mm.
- *Texture*.—Glabrous, moderate thorns.
- *Approximately density/quantity of thorns*.—Approximately 2 per linear cm.
- *Color*.—Near Red-Purple 59A.

Branches—old wood:
- *Diameter*.—Approximately 7 to 12 mm.
- *Color*.—Near Greyed-Green 195B.
- *Texture*.—Rough thick woody striations.
- *Thorns*.—Approximately density/quantity of thorns: Approximately 2 per linear cm. Color of thorns: Immature: Red 39A. Mature: Near Greyed-Orange 165A.
- *Shape*.—Deltoid, moderately hooked.
- *Height*.—Average 4 to 6 mm.
- *Diameter*.—Base near 5 mm. Tip near 0.2 cm.

FOLIAGE

Leaf:
- *Arrangement*.—Alternate and compound.
- *Quantity*.—Average 12 per main branch.
- *Internode*.—Average range 1.5 to 2.2 cm.
- *Average length*.—Approximately 8.0 cm.
- *Average width*.—Approximately 4.4 cm.

Rachis:
- *Average length*.—Approximately 2.5 cm.
- *Average diameter*.—Approximately 0.2 cm.
- *Color*.—Near RHS Yellow-Green 144A.
- *Texture*.—Upper surface glabrous. Lower surface glabrous with infrequent microthorns.

Leaflet:
- *Quantity*.—3 or 5 per leaf.
- *Average length*.—Approximately 3.0 cm.
- *Average width*.—Approximately 2.2 cm.
- *Shape of blade*.—Ovate.
- *Apex*.—Acute.
- *Base*.—Rounded.
- *Margin*.—Serrate.
- *Appearance of top surface*.—Very glossy.
- *Appearance of bottom surface*.—Matte.
- *Texture of top surface*.—Glabrous.
- *Texture of bottom surface*.—Glabrous.
- *Color*.—Young foliage upper side: Near Green 137A. Young foliage under side: Near Green 138A. Mature foliage upper side: Near Green 137A. Mature foliage under side: Near Green 137D.
- *Venation*.—Type: Reticulate. Venation color upper side: Near Yellow-Green 144C. Venation color under side: Near Yellow-Green 144C.

Petiole:
- *Average length*.—Approximately 2.0 cm.
- *Average diameter*.—Approximately 0.2 cm.
- *Color*.—Near Yellow-Green 144B.
- *Texture*.—Glabrous.

FLOWER

Natural flowering season: Early Spring until Autumn.
Inflorescence type and habit: Single occurring full rotate flowers.
Rate of flower opening: Approximately 4 days from bud to fully opened flower.
Flower longevity on plant: 10 to 14 days, after fully opened.
Quantity of flowers: 10 to 20 fully opened flowers and buds.

Flower size:
- *Diameter*.—Approximately 7 cm.
- *Height*.—Approximately 4 cm.

Peduncle:
- *Length*.—3.0 cm.
- *Diameter*.—0.3 cm.
- *Color*.—Near RHS Yellow-Green 144C, flushed 187B.

Petals:
- *Petal arrangement*.—Multiple rotate, overlapping whorls.
- *Petal quantity*.—90 to 110.
- *Length*.—3.5 cm.
- *Width*.—3.0 cm.
- *Shape*.—Broad deltate.
- *Margin*.—Entire, slightly ruffled.
- *Apex*.—Rounded.
- *Base*.—Broad attenuate.
- *Texture*.—Glabrous all surfaces.

Color: Petals.
- *When opening*.—Upper surface: Upper section near Red 49A, center section near 49B, base near 49D. Lower surface: Upper section near Red 55C, center section near 55D, base near 56D. Basal blotch White 155A.
- *Fully opened*.—Upper surface: Near RHS Red 55D. Lower surface: Near RHS Red 55D. Color Changes when aging, both surfaces: Upper section near Red 56A and 56B, large center blotch and base near White 155A.

Bud:
*Shape*.—Ovate.
*Length*.—Approximately 2.2 cm.
*Diameter*.—Approximately 1.8 cm.
*Color*.—Near Red 49B.

Sepals:
*Quantity*.—5.
*Length*.—2.1 cm.
*Width*.—1.0 cm.
*Shape*.—Deltoid.
*Apex*.—Apiculate.
*Margin*.—Entire, with long awn-like structures emerging from sides.
*Color*.—Interior Surface: Near Green RHS 138B. Exterior Surface: Near Green RHS 137C.
*Texture*.—Minutely pubescent upper and lower surfaces.

Receptacle:
*Length*.—1.1 cm.
*Width*.—0.7 cm.
*Shape*.—Flattened dome.
*Color*.—Near RHS Green 143D.

Fragrance: Moderately strong, rose fragrance.

REPRODUCTIVE ORGANS

Stamens:
*Quantity*.—Average range 40 to 50.
*Filament length*.—Approximately 0.5 to 0.7 cm.
*Filament color*.—Near Yellow 4C.

Anthers:
*Length*.—0.2 cm.
*Shape*.—Narrow globular.
*Color*.—Near Yellow-Orange 17A.
*Pollen*.—Color: Yellow-Orange 17A. Quantity: Scant.

Pistil:
*Number*.—Approximately 30 to 50.
*Pistil length*.—Approximately 1.2 cm.
*Style*.—Length: Approximately 0.4 cm. Color: Near Green-Yellow 1D.
*Stigma*.—Shape: Linear. Color: Near Yellow-Green 144D.
*Ovary color*.—Near RHS Yellow-Green 144D.
*Ovary shape*.—Oblong.
*Ovary length*.—Average 0.5 cm.
*Ovary diameter*.—Average 0.2 cm.

OTHER CHARACTERISTICS

Seeds and fruits: Fruits approximately 1.8 in length and 1.8 cm diameter. Colored near Orange 28A. Approximately 50 to 100 seeds. Seeds approximately 5 mm long, 4 mm wide. Colored near Brown 200D.

Disease/pest resistance: Good overall disease resistance to normal pests and diseases typical of garden roses.

What is claimed is:

1. A new and distinct garden floribunda cultivar of *Rosa* plant named 'LIMbird' as herein illustrated and described.

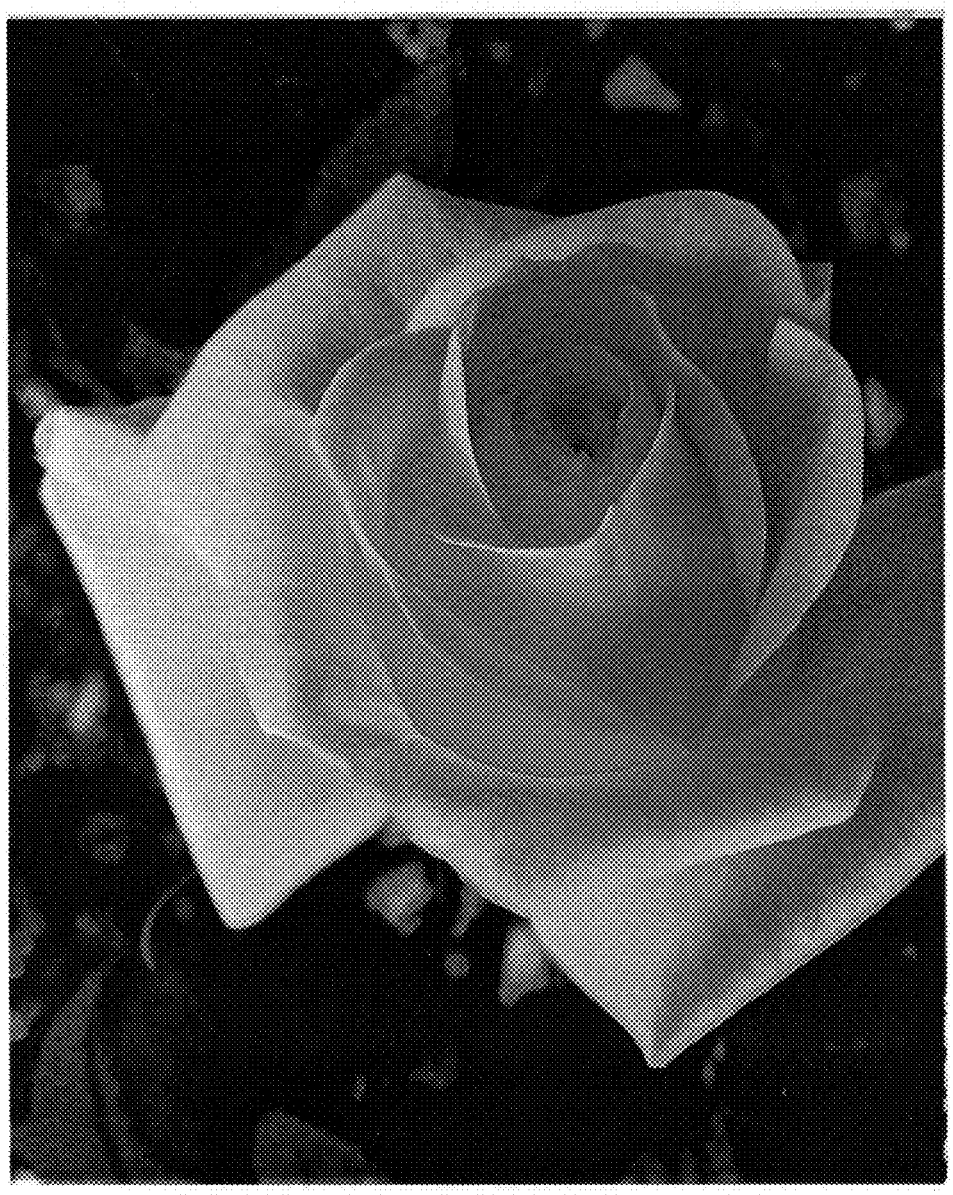

* * * * *